(12) United States Patent
Gramnäs

(10) Patent No.: US 6,596,029 B1
(45) Date of Patent: Jul. 22, 2003

(54) FOOT PROSTHESIS

(75) Inventor: Finn Gramnäs, Hästskovägen (SE)

(73) Assignee: Gramtec Innovation AB, Kinna (SE)

( * ) Notice: Subject to any disclaimer, the term of this patent is extended or adjusted under 35 U.S.C. 154(b) by 0 days.

(21) Appl. No.: 10/030,589

(22) PCT Filed: Jul. 10, 2000

(86) PCT No.: PCT/SE00/01475

§ 371 (c)(1),
(2), (4) Date: Jan. 4, 2002

(87) PCT Pub. No.: WO01/06965

PCT Pub. Date: Feb. 1, 2001

(30) Foreign Application Priority Data

Jul. 9, 1999 (SE) .................................. 9902653

(51) Int. Cl.⁷ .................................. A61F 2/66
(52) U.S. Cl. .................................. 623/55
(58) Field of Search .................. 623/53, 55, 54, 623/56

(56) References Cited

U.S. PATENT DOCUMENTS

| | | | | |
|---|---|---|---|---|
| 4,364,128 A | * | 12/1982 | Mummert | 623/53 |
| 5,571,210 A | * | 11/1996 | Lindh | 623/38 |
| 6,165,228 A | * | 12/2000 | Lindh | 623/55 |

* cited by examiner

Primary Examiner—Corrine McDermott
Assistant Examiner—Will H Matthews
(74) Attorney, Agent, or Firm—Gardner Carton & Douglas LLC

(57) ABSTRACT

The present invention relates to a foot prosthesis comprising a front foot portion (1), a rear foot portion (2) and an intermediate foot portion (3) formed by a number of rods (8) of resilient material, which rods extend in the longitudinal direction of the foot prosthesis. According to the invention the rods (8) are rotatably connected with at least one of the front and rear foot portions (1,2).

8 Claims, 2 Drawing Sheets

FOOT PROSTHESIS

TECHNICAL FIELD

The present invention relates to a foot prosthesis comprising a front foot portion, a rear foot portion and an intermediate foot portion formed by a number of rods of flexible and resilient material, which rods extend in the longitudinal direction of the foot prosthesis.

BACKGROUND OF THE INVENTION

A foot prosthesis of the above mentioned type is known through WO 98/01092. In the known foot prosthesis, the rods are fixed to the front and rear foot portions. A such prosthesis functions well during use on an even ground but worse on an irregular ground where the different portions may need to pivot relative each other around longitudinal axes.

The present invention aims to improve a foot prosthesis of the above mentioned type so that the different foot portions can be easily rotated relative each other around longitudinal axes and to provide a foot prosthesis which characteristics can be easily adjusted to the needs of different users.

SUMMARY OF THE INVENTION

These aims are achieved by a foot prosthesis comprising a front foot portion, a rear foot portion and an intermediate foot portion formed by a number of rods of resilient material, which rods extend in the longitudinal direction of the foot prosthesis, characterized in that the rods are rotatably connected to the front and rear foot portions. By the rotatable connection of the rods, a rotation of the front and rear foot portions relative each other is not hindered by torsion forces from the rods, but are only exposed to bending forces. Besides facilitating rotation of the prosthesis portions relative each other it is easy to ad just the characteristics of the foot prosthesis to different users as the only thing that has to be taken into consideration in such an adjustment is the bending resistance of the rods. Nor will the rods exert any torsional force to the material in the connections to the front and rear foot portions, which eliminates the risk of endurance failure in these connections.

In a preferred embodiment the front and rear foot portions comprise sleeves of low friction material for receiving the rods and the rods have a circular cross section. At least one of the rods can have a different bending resistance from the other rods. The rear foot portion comprises an elongated element, which protrudes above the rods and which is vertically located at a distance above the rods in their resting position and which restricts the bending deformation of the rods. Further, the foot prosthesis comprises a cover of flexible material, which surrounds the foot portions so that axial displacement of the front and rear foot portions relative each other is substantially prevented and the rear foot portion comprises a heel section, which is rotatable around a central, longitudinal axis. Advantageously, the heel section comprises an element of resilient material, which extends between a lower heel plate and an upper part of the rear foot portion.

LIST OF DRAWINGS

In the following the invention will be described with reference to enclosed figures, in which.

DESCRIPTION OF A PREFERRED EMBODIMENT

Figure 2:
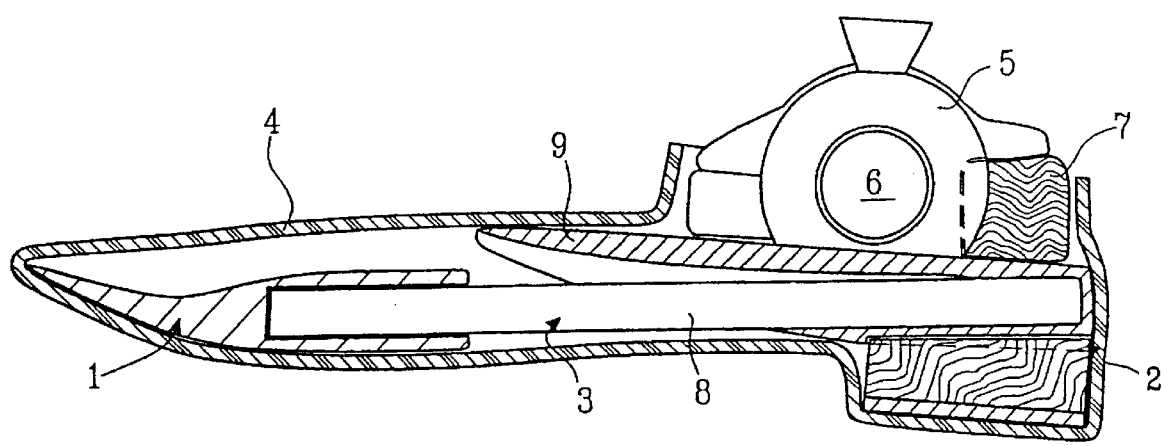
FIG. 2 shows a side view, partly in section, of the foot prosthesis in FIG. 1.

The foot prosthesis shown in the figures comprises a front foot portion 1, a rear foot portion 2, an intermediate foot portion 3 and a cover 4 surrounding these portions, so called foot cosmetics. The rear foot portion 2 is connected with an ankle 5 via an articulated axle 6. Further, the foot prosthesis is provided with a body 7 of resilient material, which bears on a part of the ankle 5 and admits a limited pivoting movement of the lower part of the leg relative the foot prosthesis around the articulated axle 6 against the effect of the spring force of the body 7. In the initial position shown in FIG. 2 i.e. in a position in which the foot prosthesis is unloaded, a front portion of the ankle is bearing on a rest at the foot prosthesis. The ankle also comprises elements to allow a step-less adjustment in the initial position of the angle between the foot prosthesis and the lower part of the leg of a prosthesis wearer. Preferably, these elements are constituted by a chamber filled with hydraulic fluid and provided with two inlets, which are connected with each other by means of a valve-controlled transfer pipe. In this chamber a partition wall extends which is connected to the ankle, which wall is displacable in the chamber when the transfer pipe is opened, but stationary when the transfer pipe is closed. An ankles which cooperates with a foot prosthesis in the above described way is known through WO 96/25898 and do not constitute any part of the present invention. For more details on the design of a such ankle, it is referred to that document. Other types of ankles can of course be used with the foot prosthesis according to the invention and the described ankle only constitutes a preferred, suitable choice of ankle.

The intermediate foot portion 3 comprises a number of rods 8 of flexible and resilient material, e.g. glass fibre. In the shown embodiment the foot portion 3 is made up of four glass fibre rods 8. The rods 8 have a circular cross section and are inserted in recesses in the front and rear foot portions 1 and 2. The fit between the rods and the recesses is such that the rods are rotatable in the recesses and can easily be removed from or inserted in these. If, for instance, the front foot portion 1 has to rotate itself around a longitudinal axis, for example if the prosthesis wearer with its front foot portion would step on a stone or any other irregularity on the ground, relative the rear foot portion 2 this means, both that the front foot portion has to rotate around a longitudinal axis, which results in that the front foot portion has to rotate around each rod, and that the rods have to individually bend itself to permit the rotation of the front foot portion. By the fact that the rods can rotate in its recesses, this can be done without the rods exerting torsion forces on the front foot portion, and by the rods being also axially displacably mounted in the recesses, the rotation of the front foot portion can be performed without the different bending of the rods forces the front foot portion to rotate around a vertical axis.

By the rods being displacable in its recesses in the rotational direction as well as in the axial direction, the rods are exposed to almost only bending loads during a rotation of the front foot portion relative the rear foot portion. This makes it very simple to design a foot prosthesis according to the invention so that a desired torsion resistance against rotation around longitudinal axes is obtained, as the only thing that has to be taken into consideration is the bending resistance of the rods. In addition, rods with different bending resistance can be used, which for example makes it possible to obtain different torsion resistance for relative rotation of the front foot portion in different rotation directions.

Furthermore, the rods and the front and rear foot portions will nearly be exposed to only friction forces during the relative movements between themselves, which makes the risk for endurance failure during usage of a foot prosthesis according to the invention very small. To minimize the wear it is preferred to mount the rods in the recesses so that the friction forces during rod rotation and axial displacement is small by making sure that the recesses in the front and rear foot portions are constituted by a material with a low friction coefficient, either by manufacturing the front and rear foot portions of a low friction material or by designing the recesses in sleeves of low friction material, for example Teflon, or acetal plastics, inserted in the front and rear foot portions.

There are also further advantages, than the above mentioned, with mounting the rods freely in recesses in the front and rear foot portions. By this design, it is easy to adjust the length of the foot prosthesis to the needs of the prosthesis wearer by choosing rods of suitable length or by cutting existing rods before they are inserted in its mountings. It is even very easy to change rods if the needs of the prosthesis wearer change, e.g. if the prosthesis wearer shall go hiking with a heavy backpack on the back and then needs stiffer rods than usual.

As the rods are axially displacably mounted in the front and rear foot portions, these portions need to be held together in some way in the longitudinal direction. In the shown embodiment this is accomplished by the foot cosmetics 4, which work against longitudinal movements of the front and rear foot portions relative each other. Preferably, the foot cosmetics are manufactured of a flexible and resilient material, e.g. foam of polyurethane. Another way of holding the front and rear portions together is to connect these with flexible elements, which advantageously, has a limited elasticity, e.g. textile ribbons, which on each side of the foot portions extend between these on the outside of the rods 8.

The rear foot portions 2 comprises an element 9, which protrudes forward and extends above the rods 8. The bottom surface of this element is curved and extends above the rods at a distance which in the unloaded position of the foot prosthesis successively increases in the direction of the front foot portion 1. The element 9 delimits the upward bending of the rear foot portion 2 relative the front foot portion 1 and secures that the rods 8 are not bended so much that they can break. In the shown embodiment, the element 9, constitutes an integrated section of the rear foot portion, but in a variant the clement can be detachably mounted to the rear foot portion. A such variant allows exchange of the element 9 and thereby allowing variation of the maximum upward bending of the rear foot portion by said exchange of the element 9 with another clement with another curvature on its bottom surface.

Figure 1:
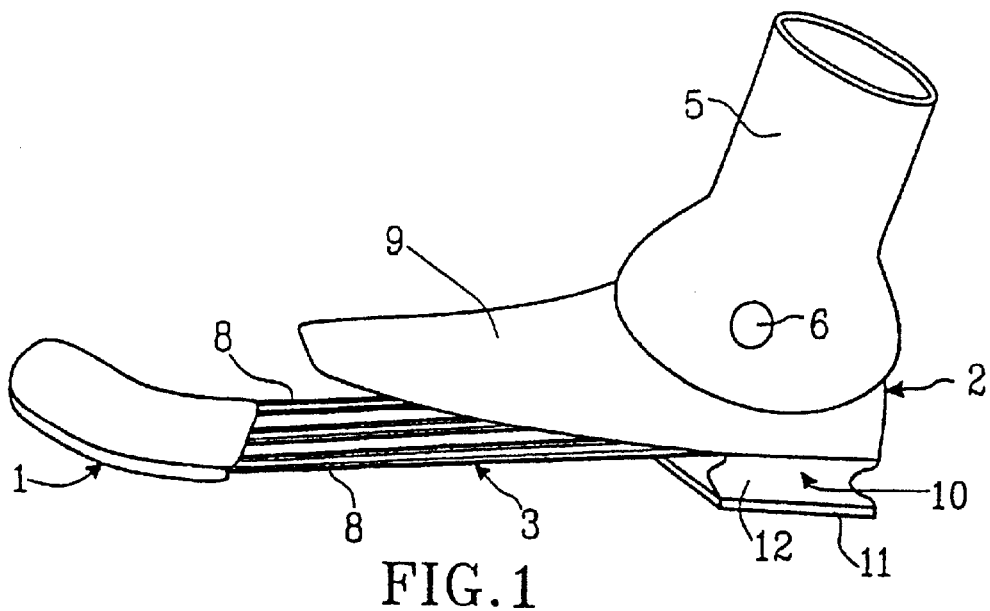
FIG. 1 shows a view in perspective of a foot prosthesis according to a preferred embodiment of the invention with the foot cosmetics removed.
Figure 3:
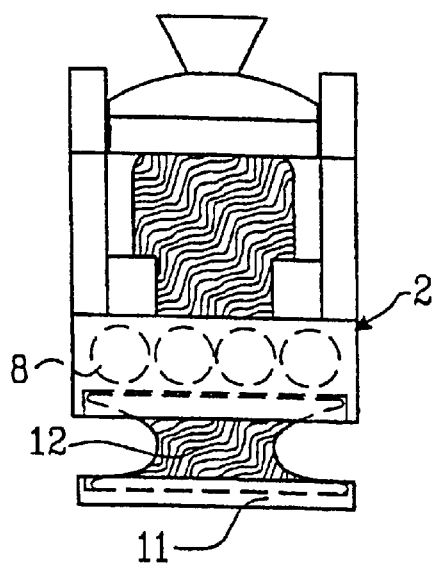
FIG. 3 shows a view from the back of the foot prosthesis in FIG. 1.
Figure 4:
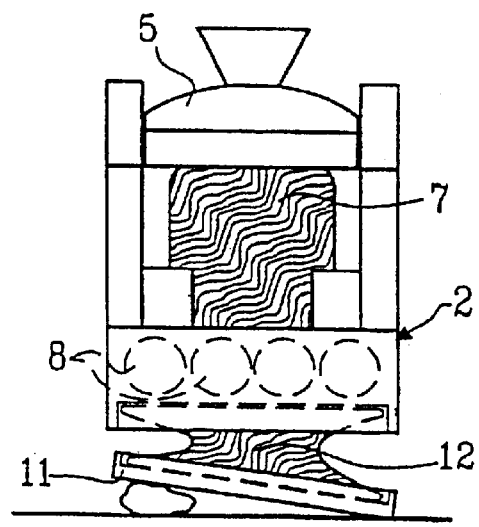
FIG. 4 shows a view corresponding to FIG. 3, but with the foot prosthesis in loaded state.

The rear foot portion 2 also comprises a heel section 10 formed from a heel plate 11 and an element 12 of resilient material, e.g. rubber, with a cross section formed as a hour-glass as seen from the back, which element 12 connects the heel plate 11 with the rest of the rear foot portion 2. Thereby, the heel plate 11 can rotate around a central, longitudinal axle relative the other parts of the rear foot portion, as indicated in FIG. 4.

Preferably, the front and rear foot portions are manufactured of thermoplastic resin reinforced with fibres, but other materials can also be used, e.g. light metals.

Naturally, the described embodiment can be modified in several ways within the scope of the invention, specially with respect to the choice of material for the different parts. The rods can for example be manufactured of carbon/graphite fibres or glass fibres held together with thermosetting resin or thermoplastic resin. Furthermore, the rods can have a form other than straight, e.g. when using high heeled shoes, the front end portions of the rods can constitute an angle to the rest of the rods. If the rods are mounted in sleeves of low friction material, the rods can have other cross sections than circular assuming that the sleeves have a rotationally cylindric outside. The rods do not need to be arranged in a linear row, as shown in the embodiment, but can be provided in one or several curved rows. The element 9 do not need to have a curved form, but can simply be constituted by a stop element, which during a certain bending prevents additional bending of that rod or these rods that have been bent to the stop position. The invention shall only be limited by the contents of the accompanying claims.

What is claimed is:

1. A foot prosthesis comprising a front portion, a rear foot portion and an intermediate foot portion formed by a number of rods of resilient material, the foot prosthesis having a longitudinal direction extending between the front portion and the rear foot portion, which rods extend in the longitudinal direction of the foot prosthesis, the foot prosthesis having a longitudinal axis that is generally parallel to the longitudinal direction, characterized in,
that the rods are rotatably connected with the front and rear foot portions such that the front portion and the rear foot portion rotate independently of one another around the longitudinal axis.

2. The foot prosthesis according to claim 1,
characterized in,
that the front and rear foot portions, which the rods are rotatably connected with, comprise sleeves of low friction material for receiving the rods.

3. The foot prosthesis according to claim 2,
characterized in,
that the rods have a circular cross section.

4. The foot prosthesis according to claim 2,
characterized in,
that at least one of the rods has a different bending resistance than the other rods.

5. The foot prosthesis according to claim 1,
characterized in,
that the rear foot portion comprises an elongated element which protrudes above the rods and which is vertically located at a distance above the rods in their resting position and which restricts the bending deformation of the rods.

6. The foot prosthesis according to claim 1,
characterized in,
that the foot prosthesis comprises a cover of flexible material, which surrounds the front portion, the rear foot portion, and the intermediate foot portion so that axial displacement of the front and rear foot portions relative to each other is substantially prevented.

7. The foot prosthesis according to claim 1,
characterized in,
that the rear foot portion comprises a heel section, which is rotatable around a central, longitudinal axis that is generally parallel to the longitudinal direction.

8. The foot prosthesis according to claim 7,
characterized in,
that the heel section comprises an element of resilient material, which extends between a lower heel plate and an upper part of the rear foot portion.

* * * * *